United States Patent [19]

Reich

[11] Patent Number: 4,609,874
[45] Date of Patent: Sep. 2, 1986

[54] SYSTEM FOR MONITORING PH IN OIL IN WATER LIQUIDS

[75] Inventor: Ronald A. Reich, Aspinwall, Pa.

[73] Assignee: Aluminum Company of America, Pittsburgh, Pa.

[21] Appl. No.: 569,968

[22] Filed: Jan. 11, 1984

[51] Int. Cl.[4] ............................................. G01N 27/56
[52] U.S. Cl. ................................ 324/438; 137/624.13; 137/624.18; 204/402; 204/409
[58] Field of Search ........................ 324/438, 439, 450; 204/402, 409, 433; 137/624.13, 624.18; 222/148; 72/201; 73/53, 60.1

[56] References Cited

U.S. PATENT DOCUMENTS 3,616,272 10/1971 Goerg et al. ........................ 324/438
3,681,025 8/1972 Dalgaard ............................ 23/230 R
4,151,255 4/1979 Capuano et al. .................... 324/438

Primary Examiner—Stewart J. Levy
Assistant Examiner—Kevin D. O'Shea
Attorney, Agent, or Firm—Elroy Strickland; John P. Taylor

[57] ABSTRACT

An improved system for the monitoring of pH of a liquid containing oil and water by directing the flow of at least a portion of the liquid into contact with the electrode of a pH meter for measuring the pH of the liquid, interrupting the flow of liquid to the electrode periodically, directing the flow of a washing solution into contact with the electrode to remove any depositions on the electrode, and then resuming the flow of the liquid into contact with the electrode to continue the monitoring of pH of the liquid without the need for manual removal and cleaning of the glass electrode.

18 Claims, 3 Drawing Figures

SYSTEM FOR MONITORING PH IN OIL IN WATER LIQUIDS

BACKGROUND OF THE INVENTION

This invention relates to pH measurements. More particularly, this invention relates to a system for measuring the pH of a liquid containing oil and water.

In metalworking operations, such as, for example, rolling of a hot metal, such as aluminum, in a rolling mill, a liquid is applied to the rolls and/or the rolled stock which functions both as a coolant and a lubricant. Commonly such a liquid comprises an oil in water mixture wherein the oil may comprise a common lubricating oil or a mixture of oil and additives blended to achieve particular properties. In any event, it is important that the oil, which functions as the lubricant, remain dispersed in the water phase. However, during the course of use, such a coolant commonly becomes contaminated due to the introduction of metal ions and formation of products of oxidation, thermal and biological degredation. Such contamination may cause the pH of the coolant to change in an undesirable way resulting in the loss of lubricating properties. It is, therefore, desirable to monitor the pH of the coolant as it is used.

As is well known to those skilled in the art, normal pH measurements involve the immersion of a glass electrode attached to a pH meter into the liquid to be tested. However, the use of such a pH meter for the measurement of the pH of an oil in water mixture is complicated by the fouling of the glass electrode by deposition of a coating of oil on the surface of the electrode, thus upsetting the measurement. When such an arrangement is used, it is, therefore, necessary to periodically disassemble the apparatus to manually clean such depositions off the glass electrode. It would, therefore, be desirable to have a system whereby the pH of an oil in water mixture can be monitored without the need for periodic manual disassembly of the monitoring apparatus to clean the glass electrode.

SUMMARY OF THE INVENTION

It is, therefore, an object of the invention to provide an improved system for the monitoring of pH of a liquid containing oil and water.

It is another object of the invention to provide an improved system for the monitoring of pH of a liquid containing oil and water wherein a coating of oil on the electrode of a pH meter may be periodically removed without the need for manual disassembly of the monitoring system.

It is yet another object of the invention to provide an improved system for the monitoring of pH of a liquid containing oil and water wherein a coating of oil on the electrode of a pH meter may be periodically removed by periodic flushing of the electrode assembly with a cleaning fluid and without the fluid contaminating the oil in water mixture.

It is yet a further object of the invention to provide an improved system for the monitoring of pH of a liquid containing oil and water wherein a coating of oil on the electrode of a pH meter may be periodically removed using a system wherein a cleaning fluid is automatically flushed through the electrode at timed periodic intervals.

These and other objects of the invention will be apparent from the description and accompanying drawings.

In accordance with the invention, an improved system for the monitoring of pH of a liquid containing oil and water comprises directing the flow of at least a portion of the liquid into contact with the electrode of a pH meter for measuring the pH of the liquid, interrupting the flow of liquid to the electrode periodically, directing the flow of a washing solution into contact with the electrode to remove any depositions on the electrode, and then resuming the flow of the liquid into contact with the electrode to continue the monitoring of pH of the liquid without the need for manual removal and cleaning of the glass electrode.

DESCRIPTION OF THE PREFERRED EMBODIMENT

Figure 1:
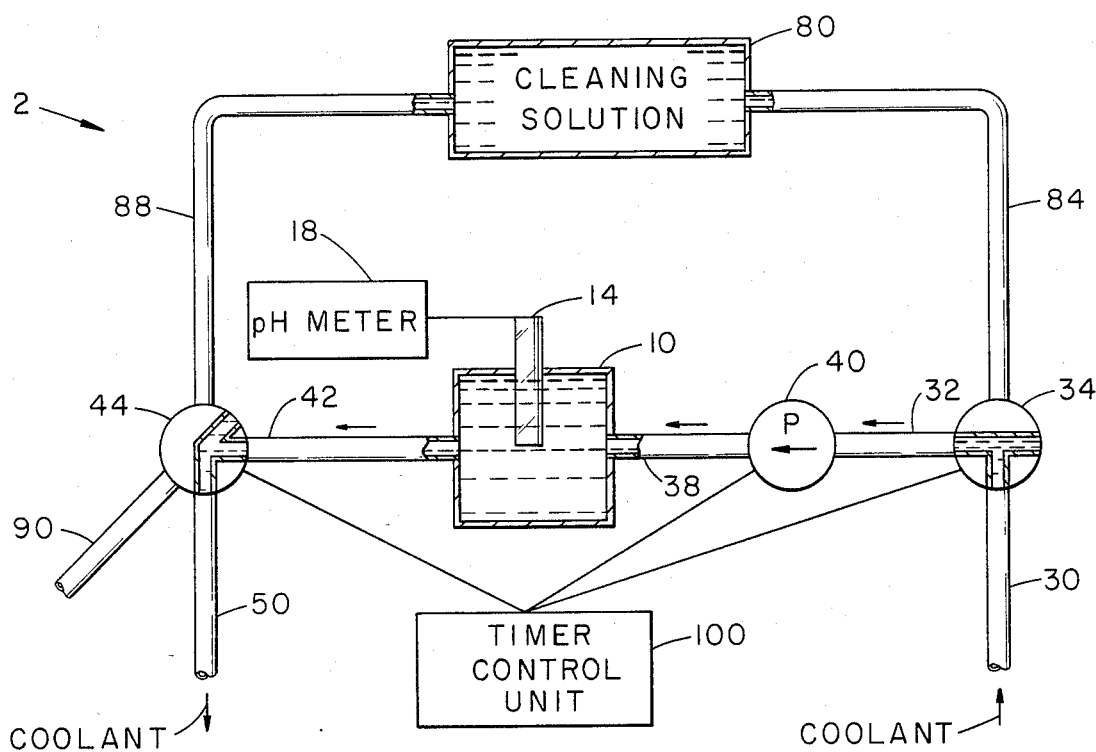
FIG. 1 is a schematic diagram illustrating the normal flow of a coolant liquid containing oil and water in contact with the electrode of a pH meter.

The monitoring system of the invention is generally shown at 2 in FIG. 1. The system generally comprises a pH cell 10 containing a glass electrode 14 which is in electrical communication with a monitoring device, such as pH meter 18. The coolant, comprising an oil in water mixture from an external source (not shown), is monitored for pH change by flowing the coolant through pipe 30 into solenoid valve 34 which, in the position shown in FIG. 1, directs the flow of the coolant into pump 40 via pipe 32. The coolant is pumped, via line 38, into the pH cell 10 where the pH is measured by contact with glass electrode 14. The coolant then exits pH cell 10 via pipe 42 and enters solenoid valve 44 which, in the position shown in FIG. 1, directs the flow of coolant back to the external source via pipe 50.

With valves 34 and 44 in the positions shown in FIG. 1, the coolant will normally flow through the pH cell for an extended period of time permitting constant monitoring of the pH of the coolant. This permits minor adjustments to the pH should it change due to use of the coolant. For example, when the coolant is used as a coolant-lubricant in a rolling mill for the rolling of hot metals, such as aluminum, a change in pH, due to accumulation of degradation products, can be adjusted for by the addition of acid or base to the coolant-lubricant.

Figure 2:
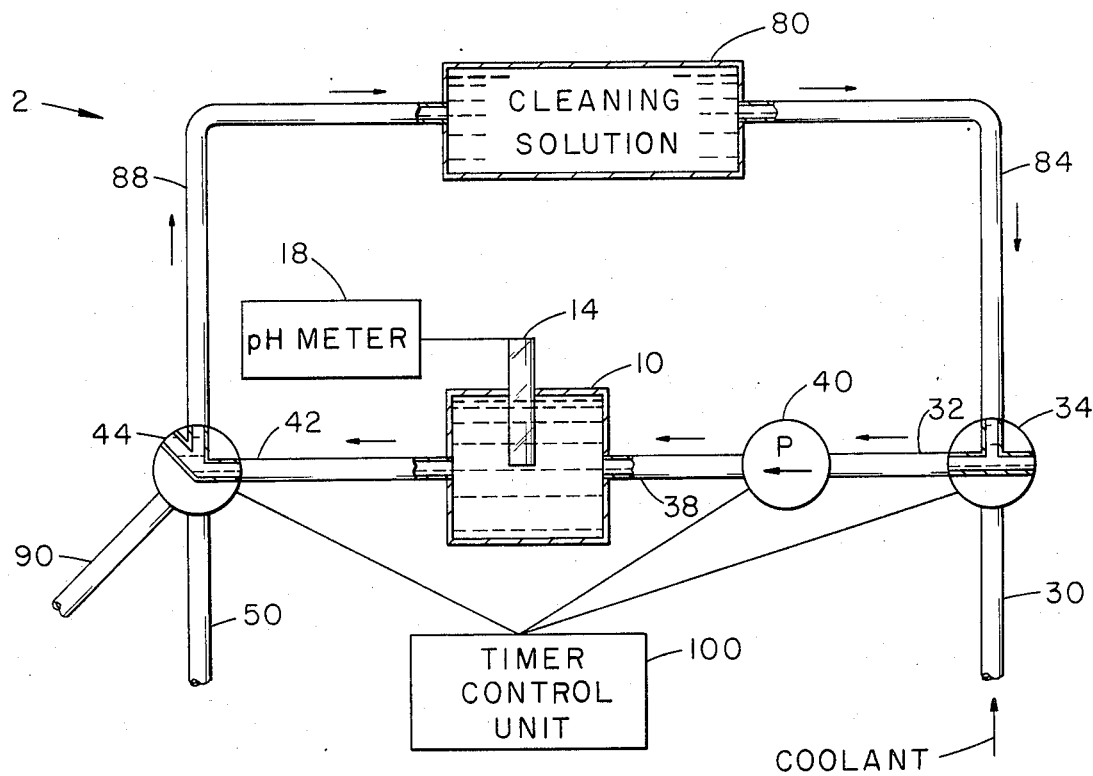
FIG. 2 is a schematic diagram showing the flow of a washing solution through the pH meter.

However, as previously discussed, the continued flow of a liquid containing oil through pH cell 10 can ultimately result in deposition of minor amounts of oil on glass electrode 14 which will result in erroneous readings of the pH of the liquid. Therefore, as shown in FIG. 2, in accordance with the invention, glass electrode 14 is periodically cleaned to remove such coatings of oil on glass electrode 14. As shown in FIG. 2, at periodic intervals valves 34 and 44 are moved to a second position whereby a cleaning solution, such as sodium hydroxide, in the illustrated embodiment, from a source 80 passes via line 84 into valve 34. Valve 34, in the position illustrated in FIG. 2, then passes this cleaning solution from pipe 84 into pipe 32 from whence it is pumped into pH cell 10 to clean off electrode 14 by forming an emulsion with the oil deposited on electrode 14. The cleaning solution then exits pH cell 10 via line 42 into valve 44. Valve 44, in the position shown in FIG. 2, circulates the cleaning solution back to the cleaning solution source 80 via pipe 88. This cleaning operation is carried out for a predetermined period of time, for example, for five minutes every two hours or five to fifteen minutes once a day.

Figure 3:
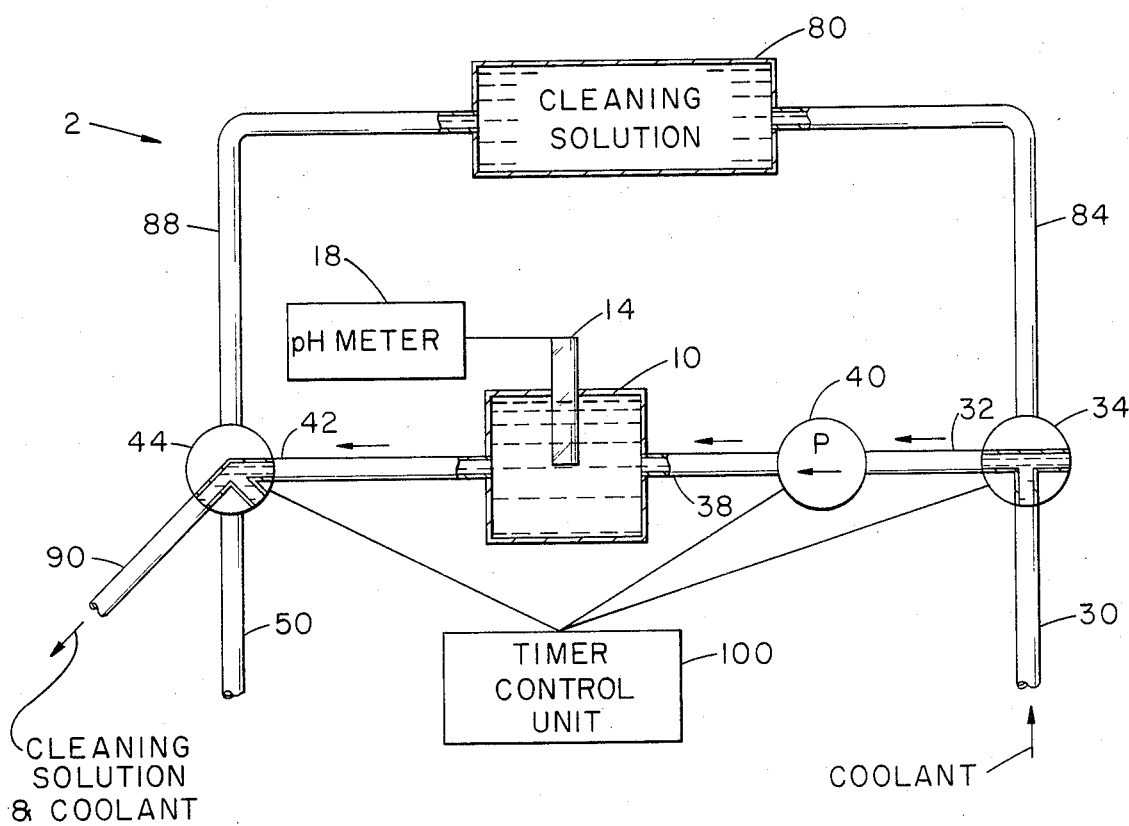
FIG. 3 is a schematic diagram illustrating flushing the washing solution out of the pH meter prior to resumption of the flow of liquid through the meter.

After the desired flushing period has expired, valve 44 may be set to a third position, as shown in FIG. 3. This position permits flushing out of pump 40, pH cell 10, and pipes 32, 38 and 42 of the cleaning solution before resuming the flow of coolant through the system, as shown in FIG. 1. In the illustrated embodiment shown in FIG. 3, valve 34 is returned to the initial position permitting coolant to flow into pump 40 to assist in the flushing process as well as to eliminate possible cavitation problems with pump 40. In another embodiment, valve 34 may be placed in an off position whereby neither coolant nor cleaning solution pass through valve 34 into pump 40, and pump 40 merely pumps out any remaining liquids in the pump, cell 14 and lines 38 and 42. In either event, the actual flushing operation is only carried on for a brief period of time ranging from a few seconds to two to three minutes. At the end of this time, valve 44 is returned to the position as shown in FIG. 1; and valve 34, if it is in an off position during the flushing operation, is also returned to the position shown in FIG. 1; and circulation of the cooling system and monitoring of its pH is resumed.

Whether or not the flushing step is used, the cleaning solution may be periodically replenished or replaced in reservoir 80, depending on the periodicity of the washing cycle which, in turn, will be directed by the frequency of the fouling of electrode 14 by oil deposition.

A timer control unit 100, which may comprise a simple electrochemical timer or a microprocessor, controls the activation of solenoid valves 34 and 44 as well as pump 40. The timing unit may be set to provide for one cleaning period per day of, for example, about 10 to 15 minutes in duration, followed by the brief flushing period previously described. Alternatively, the timer may be preset to provide for a cleaning period of, for example, five minutes every two hours if the fouling of the electrode 18 warrants such frequent intervals of cleaning.

Thus, the invention provides a novel system whereby continuous monitoring of the pH of a liquid, such as an aqueous coolant containing an oil, which may deposit on the glass electrode of the pH meter may be operated on a continuous basis using an automated cleaning cycle wherein a cleaning solution is circulated through the pH meter to clean off the electrode followed by a flushing out of the cleaning solution prior to resumption of circulation of the coolant through the pH meter for continuous monitoring of the pH of the coolant-liquid. Using the system of the invention, the need for periodic and frequent interruption of the pH monitoring to disassemble and clean out the cell, including cleaning of the glass electrode, is eliminated by the use of the system of the invention.

Having thus described the invention, what is claimed is:

1. An improved method for the continuous monitoring of a liquid containing oil and water which comprises the steps of:
   (a) continuously directing the flow of at least a portion of said liquid into contact with the electrode of a pH meter to permit continuous monitoring of the pH of said liquid;
   (b) interrupting the continuous flow of said liquid to the electrode periodically;
   (c) circulating the flow of a washing solution from a source into contact with said electrode and back to said source while the flow of said liquid is interrupted to remove any coating of oil on said electrode deposited on said electrode by contact with said liquid; and
   (d) resuming the flow of said liquid into contact with said electrode to resume the continuous monitoring of pH without the need for manual removal and cleaning of said electrode.

2. The method of claim 1 including the further step of flushing said washing solution out before resuming the flow of said liquid into contact with said electrode.

3. The method of claim 1 which includes the further step of activating valve means to alternatively direct said liquid said washing solution into contact with said electrode.

4. A method for continuously monitoring the pH of a coolant comprised of oil and water which is employed in metalworking comprising the steps of:
   (a) continuously directing the coolant to and through a meter for monitoring the pH of the coolant;
   (b) measuring the pH of the coolant with said meter;
   (c) providing, from a washing solution source, a washing solution capable of emulsifying the oil of the coolant to thereby remove any deposits of oil from said meter which can result in erroneous meter readings;
   (d) periodically interrupting the flow of the coolant to the meter;
   (e) thereafter circulating the washing solution from said washing solution source to and through the meter and back to said source to emulsify and remove oil deposits from the meter;
   (f) thereafter interrupting the flow of the washing solution to the meter; and
   (f) resuming the continuous flow of coolant to and through the meter.

5. The method of claim 4 in which the washing solution is directed from the system after the meter has been cleaned by the solution and before the coolant is directed again to the meter.

6. The method of claim 4 in which the continuous flow of coolant to the meter is interrupted after a predetermined period of time to permit said step of directing said washing solution through said meter to remove oil deposits therein.

7. The method of claim 4 in which the flow of the washing solution to the meter is interrupted after a predetermined period of time.

8. Apparatus for monitoring the pH of a coolant employed in rolling metal in a rolling mill comprising:
   (a) pH meter means for measuring pH of said coolant;
   (b) conduit means for directing said coolant to and from said meter means;
   (c) valve means located in series with said meter means;
   (d) pump means located in series with said meter means and valve means;
   (e) a reservoir of washing solution connected in fluid communication with said valve means and in a fluid circuit that is parallel with said meter means and pump means;

(f) means for controlling the valve means to interrupt the flow of coolant to said meter means and to direct the washing solution to and through said meter means; and (g) means for discharging said washing solution from said meter means prior to resuming the flow of coolant to said meter means, said discharge means being capable of also discharging said coolant from said meter means if desired.

9. The apparatus of claim 8 in which said meter means includes an electrode that becomes coated with the oil of the coolant in the process of the coolant being directed through said meter means.

10. The apparatus of claim 8 in which said valve means comprises two valves connected in fluid communication with said meter means, with one of said valves being further connected to direct the flow of coolant or washing solution to said meter means while the other of said valves is connected to direct the flow of coolant or solution issuing from said meter means.

11. The apparatus of claim 8 wherein the washing solution is comprised of an aqueous mixture which emulsifies oil.

12. The apparatus of claim 8 wherein the washing solution is NaOH.

13. Apparatus for monitoring the pH of a liquid containing oil and water employed in rolling metal comprising:

(a) means for measuring the pH of said liquid including a cell containing an electrode in contact with said liquid;

(b) conduit means for directing said liquid to and from said cell;

(c) valve means located in series with said cell;

(d) pump means located in series with said cell and said valve means;

(e) a reservoir of washing solution connected in fluid communication with said valve means and in a fluid circuit that is parallel with said cell and said pump means;

(f) means for controlling said valve means to interrupt flow of said liquid to said cell and to circulate said washing solution to and through said cell and back to said reservoir to remove any oil deposits from said electrode in said cell; and (g) means for discharging said washing solution from said cell prior to resuming the flow of said liquid to said cell.

14. The apparatus of claim 13 wherein said valve means comprises first valve means having a first position to direct the flow of said liquid into contact with said electrode in said cell and second valve means having a first position to direct said liquid from said electrode back to a source of said liquid.

15. The apparatus of claim 14 wherein said first and second valve means each have a second position to respectively control the flow of said washing solution into contact with said electrode and back to a source of said washing solution.

16. The apparatus of claim 15 wherein a pump means direct the flow of either said liquid or said washing solution into contact with said electrode.

17. The apparatus of claim 15 wherein said second valve means have a third position permitting flushing said washing solution out before resuming the flow of said liquid into contact with said electrode.

18. The apparatus of claim 13 wherein timing means periodically interrupt the flow of said liquid into contact with said electrode and direct the flow of washing solution into contact with said electrode for a predetermined period of time before the flow of said liquid is resumed.

* * * * *